United States Patent [19]
Trudell et al.

[11] Patent Number: 5,593,393
[45] Date of Patent: Jan. 14, 1997

[54] LACRIMAL IRRIGATING CANNULA

[76] Inventors: Roger J. Trudell, 2565 Tamarack Ave., Boulder, Colo. 80304; Robert E. Prouty, 16006 E. Lehigh Cir., Aurora, Colo. 80013

[21] Appl. No.: 524,484

[22] Filed: Sep. 7, 1995

[51] Int. Cl.⁶ .................................................. A61M 25/00
[52] U.S. Cl. ........................................... 604/264; 604/294
[58] Field of Search ................................... 604/264, 272, 604/239, 216, 217, 294, 295, 280, 274

[56] References Cited

U.S. PATENT DOCUMENTS

| | | |
|---|---|---|
| 950,822 | 3/1910 | McElroy. |
| 2,154,968 | 4/1939 | Alkio ........................................ 128/348 |
| 3,216,616 | 11/1965 | Blankenship ............................... 222/47 |
| 3,388,703 | 6/1968 | Bowes ....................................... 128/221 |
| 3,540,447 | 11/1970 | Howe ........................................ 128/221 |
| 4,335,718 | 6/1982 | Calabrese ................................. 128/218 |
| 4,915,684 | 4/1990 | MacKeen et al. ..................... 604/264 X |

*Primary Examiner*—John D. Yasko

[57] ABSTRACT

A lacrimal cannula for insertion, dilation, probing, and irrigation of the lacrimal drainage system, starting with a small diameter distal end to facilitate entry into the lacrimal puncta, tapering in size to a larger diameter serving to seal the puncta as fluid is forced through the device.

4 Claims, 3 Drawing Sheets

LACRIMAL IRRIGATING CANNULA

BACKGROUND—FIELD OF INVENTION

The present invention relates to needles and cannulae in general, and in particular to a device for inserting into the lacrimal puncta and lacrimal canalicula.

BACKGROUND—DESCRIPTION OF PRIOR ART

The purpose of a lacrimal cannula is to insert into the puncta of the eye and then deeper into the lacrimal canalicula (ducts). Fluid is then forced through the cannula to force out obstructions of the ductwork, increase drainage of the tears, and to flush lacrimal implants. Lacrimal cannula, in general, are derivations of intravenous needles and catheters, similar to those described in U.S. Pat. Nos. 950,822 and 3,388,703 respectively.

In the past, all lacrimal cannula have been one single diameter (ranging from 27 gauge to 21 gauge) in size. The problem in using a single diameter cannula is that larger diameter (smaller gauge) could not be inserted into the puncta of the eye. The puncta required extensive dilation with a punctal dilating instrument, making this a two step process. If lacrimal duct probing were required, the process would essentially be three separate steps because a probing device would be required. Smaller diameter (larger gauge) could be inserted easier into the lacrimal puncta, but would allow a backflush of fluid once the irrigation procedure was initiated.

Prior insertion devices allowed for only an estimate of penetration depth into the lacrimal canalicula (which is only 10 mm in its entirety). This could result with insertion of the cannula further than desired, thus bruising the internal tissue at the end of the canalicula.

No prior art describes a lacrimal cannula with multiple diameters, however; U.S. Pat. No. 3,540,447 discloses a spinal needle in which the pointed distal end has a smaller diameter than the proximal end. It can be seen, however; that the tip is sharp and not useful for lacrimal punctal. If used for lacrimal irrigation it could cause bleeding and irritation of the lacrimal tissues. This device was designed specifically for spinal injection and also is attached directly to a very specific syringe. Furthermore, this device would require extensive modification (changing the end point to an even point versus slanted, rounding and smoothing of the sharp tip, decrease in shaft length, and several changes in diameter) to be utilized for lacrimal insertion. U.S. Pat. No. 3,216,616 discloses a reduced diameter point on a needle. This patent describes almost exclusively the improvements in syringe design and does not give specifics of the needle design. The device described would make lacrimal irrigation much more complex and would require modifications described in the patent above. U.S. Pat. No. 4,335,718 describes a two diameter needle cannula for penetration of the skin. Again, this device would require the extensive modification above to be utilized for lacrimal insertion. All the patents listed above would require a change in use to be used for lacrimal irrigation.

OBJECTS AND ADVANTAGES

Accordingly, several objects of this invention: 1) The smaller diameter tip (less than 23 gauge) allows for no need to dilate the lacrimal puncta. The process of punctal dilation and irrigation than becomes a one step process versus a two step process. 2) The unique design allows for three distinct uses: punctal dilation, lacrimal canalicula probing, and lacrimal irrigation. 3) This should potentially decrease costs of the medical system because currently there are separate (CPT) procedural billing codes for punctal dilation and lacrimal canalicula probing. This invention can perform both tasks all in one step. 4) The small diameter rounded end, is a change in shape over prior lacrimal cannula that allows for easier insertion into the lacrimal puncta. 5) The change in shape from small diameter to larger diameter prevents a backwash of irrigation fluid and allows for a higher water pressure flush of obstructed lacrimal drainage systems. 6) The known lengths of the small diameter portion of the cannula shaft and the taper allow for accurate depth of insertion into the lacrimal canalicula. 7) The device allows for practitioner choice for standard syringe mountings for use with glass, plastic, synthetic, disposable, and reusable syringes. 8) The device is ideal for removal of silicone lacrimal implants, which may be causing excessive blockage and tearing. 9) The device may prevent more complex procedures (as explained in U.S. Pat. No. 2,154,968) and/or surgery to clear plugged lacrimal systems.

Further objects and advantages of this invention will become apparent from consideration of the drawings and ensuing description.

Figure 1:
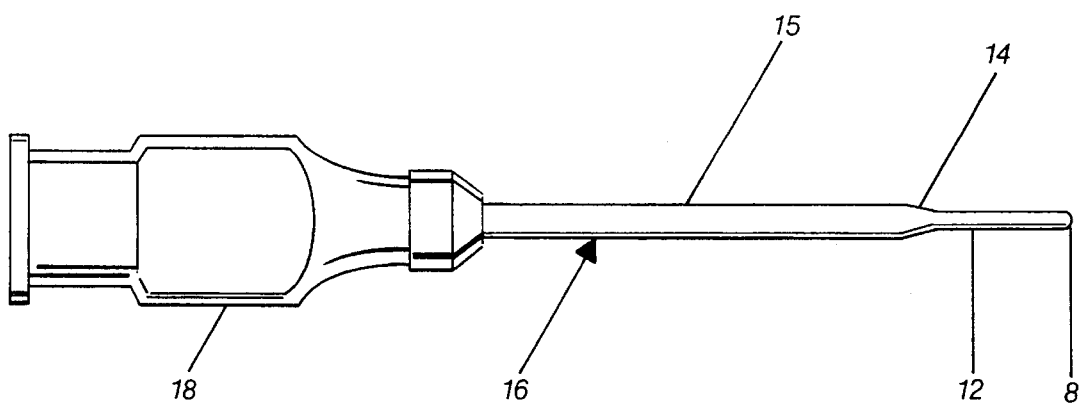
FIG. 1 shows an exterior lateral view of the lacrimal cannula showing the taper design and hub connection for standard syringe fittings.

REFERENCE NUMERALS IN DRAWINGS 8 rounded distal end
10 tube opening
12 small diameter portion of cannula shaft
14 taper
15 large diameter portion of cannula shaft
16 lacrimal cannula
18 hub
20 hollow tube
22 sidewalls of cannula shaft
24 syringe
26 syringe plunger
28 lacrimal puncta
30 lacrimal canalicula (duct)

DESCRIPTION—FIGS. 1 to 4

Shown in FIG. 1 is a lacrimal irrigating cannula device generally indicated at 16, constructed in accordance with the present invention. The lacrimal irrigating cannula 16 includes a forward distal end 8 with an opening 10 (seen in FIG. 2) to a hollow tube 20 (seen if FIG. 2) which runs the entire length of the cannula 16. An important feature of the invention is the distal end 8 which is rounded and made smooth over the width of the cannula sidewalls 22 (seen if FIG. 2) for easy and safe insertion into the tissue of the lacrimal puncta 28 (seen in FIG. 3). The cannula's distal shaft 12 begins with a small diameter (larger gauge) with a taper 14 to a larger diameter portion of the cannula shaft 15. This larger proximal end of the cannula shaft 15 is attached to a standard hub 18. The hub is for connection to standard syringe type fittings and convenient handling of the remainder of the cannula 16, and is not itself a part of the device of present invention.

Figure 2:
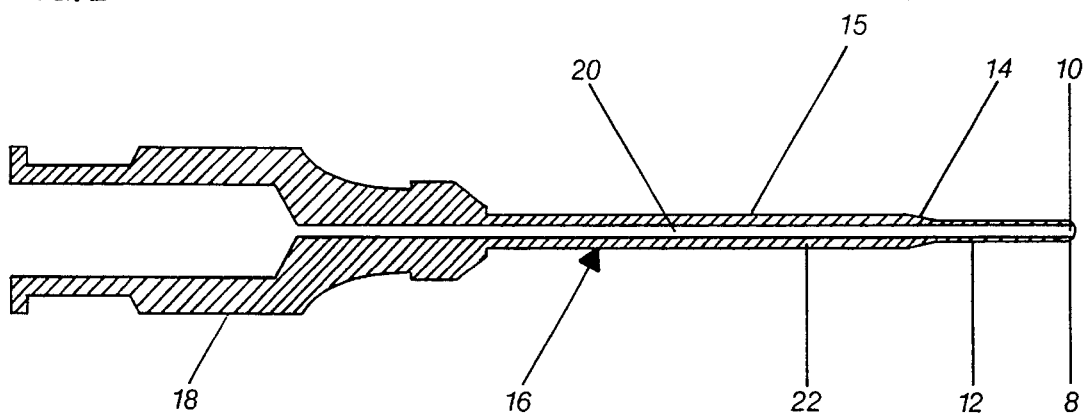
FIG. 2 is a cross-sectional view taken along the longitudinal center line of the device.

FIG. 2 shows detail of the lacrimal cannula 16 which is formed from a hollow tube 20 starting at the distal tube opening 10 extending the length of the cannula 16 with a proximal opening within the hub 18. The narrow rounded distal end 8 is made smooth over the entire width of the sidewalls 22. The point of the rounded distal end 8 is intended for easy penetration into a lacrimal puncta 28 (as seen in FIG. 4.)

Figure 3:
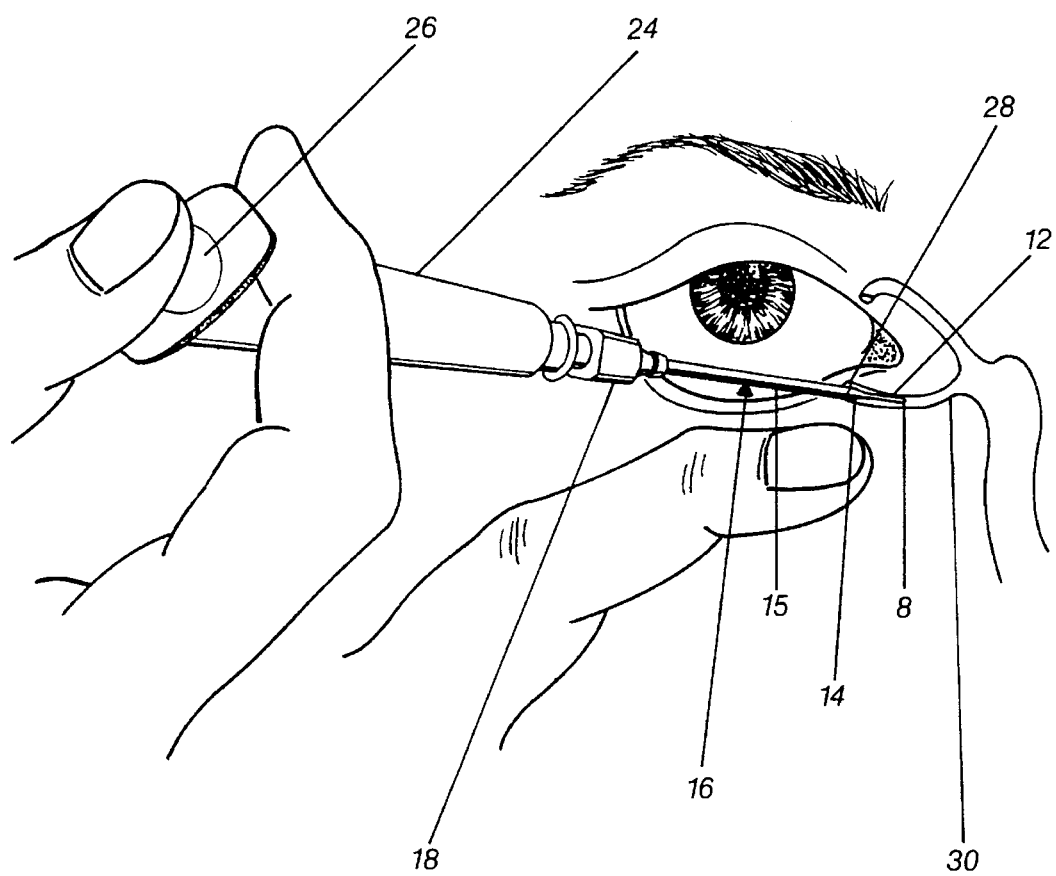
FIG. 3 shows the insertion method of the cannula into the lacrimal puncta with the cannula inserted beyond the taper point.

FIG. 3 shows a practitioner inserting the narrow rounded end 8 into the lacrimal puncta 28. The cannula hub 18 is attached to a syringe 24, which is an optional element. The syringe 24 is used for convenient handling of the remainder of the cannula 16 and insertion of fluid, and is not itself a portion of the device of the present invention. The lacrimal irrigating cannula 16 is introduced vertically into the lacrimal canalicula 30 for a length of about 2 mm. The lacrimal cannula 16 is than lowered to a horizontal position and pushed deeper into the canalicula 30. When the cannula insertion reaches the taper 14, the exact depth of insertion is known. The cannula is than inserted deeper into the canalicula 30 to the desired insertion depth. Once the cannula 16 is inserted beyond the length of the taper 14, the larger portion of the cannula shaft 15 will be tightly gripped by the sphincter action of the lacrimal puncta 28. The plunger of the syringe 26 is than depressed forcing irrigation fluid into the canalicula 30.

Figure 4:
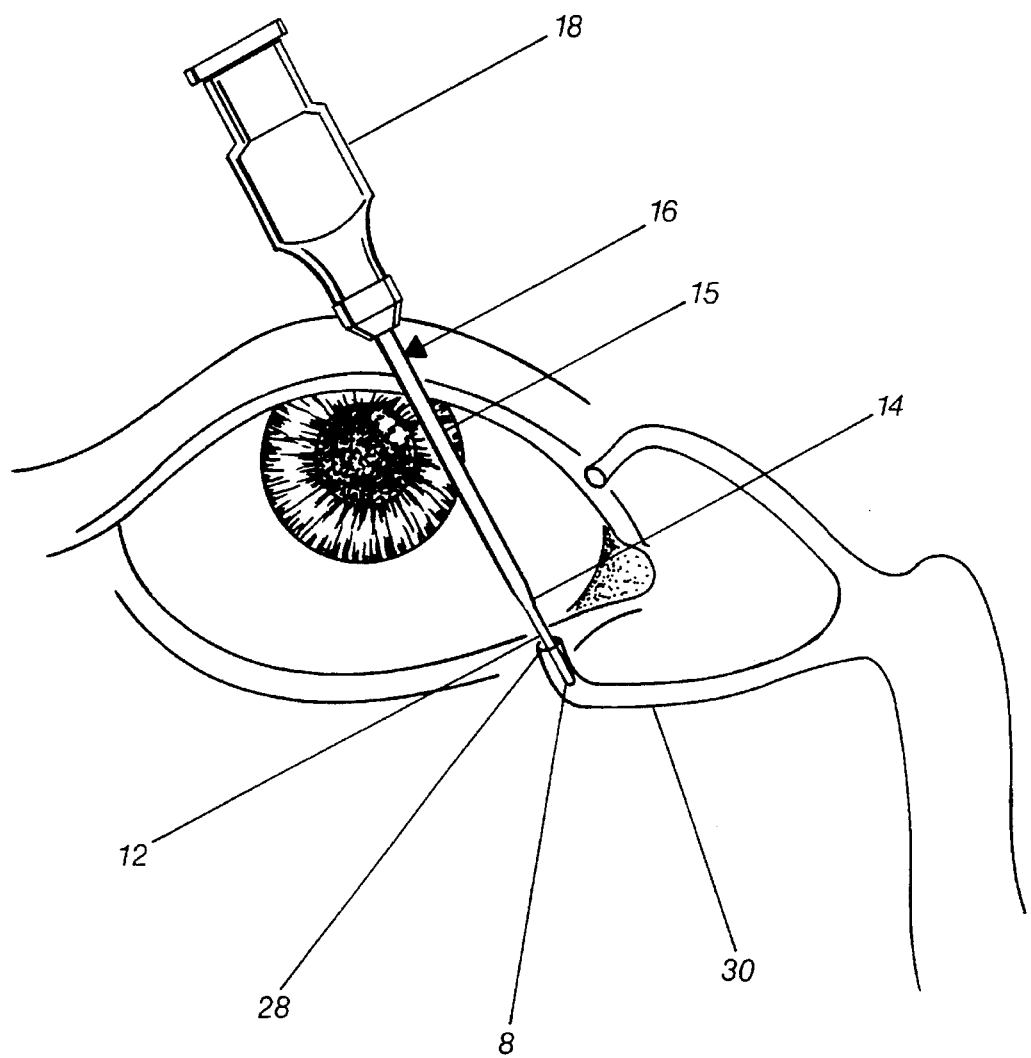
FIG. 4 shows the small diameter distal portion of the cannula being inserted into the lacrimal puncta.

FIG. 4 displays an enlarged view of the lacrimal puncta 28 with the small diameter portion of the cannula shaft 12 inserted into the lacrimal puncta 28 and lacrimal canalicula 30.

SUMMARY, RAMIFICATIONS, AND SCOPE

Thus the reader will see that the lacrimal irrigating cannula allows for an easy one step insertion (no punctal dilation is necessary) for the irrigation process or lacrimal canalicula probing. The larger diameter addition allows for closure of the lacrimal puncta to avoid backwash of fluid during the irrigation process. The device allows for the practitioner's choice of syringe type used. The design also allows for probing into the lacrimal cannalicula without using a different device.

While the above description contains many specificities, these should not be construed as limitations on the scope of the invention. Many other variations are possible, for example:

1. The cannula is preferably made of inert metal, but could also be fabricated from precious metals, other metals, plastic, natural materials, or synthetic materials.
2. The tube opening could be placed in the front, on the sides, and have multiple openings.
3. The shaft of the cannula could be curved or bent for easier insertion and/or handling.
4. Multiple tapers could be produced rather than just one taper. The shaft could also be formed in the shape of a wedge to perform the same desired results.
5. The smaller diameter of cannula shaft will generally be 26 or 27 gauge, but this could vary.
6. The length of the small diameter portion of the cannula shaft and large diameter portion can vary according to practitioner preference.
7. Taper length, taper angle, and taper positions could be made to vary according to practitioner preference.
8. The hub connection could vary in its configuration or be eliminated altogether to attach to other devices.
9. Sidewall thickness could vary to allow for reinforcement of the cannula.
10. The cannula will generally be manufactured as one connected piece, but could be made integrally or separately or in modular sections.
11. Markings (i.e. an etch mark every one or two mm) could be placed on the cannula for depth measurement.

It is understood that the present invention is not limited to the particular construction and arrangement disclosed, but embraces all such modified forms. Its scope is to be determined by the appended claims rather that by examples given.

We claim:

1. A lacrimal canaliculus insertion, dilation, probing, and irrigation device comprising:

a hollow fluid transmission tube ending in a smooth distal tip, with a tube diameter sufficiently small to insert into the lacrimal puncta, tapering to a larger proximal diameter sufficiently large enough to seal the puncta during fluid irrigation, of sufficient length to extend into the lacrimal canaliculus, whereby a practitioner could dilate a lacrimal puncta, probe, estimate depth of insertion, irrigate and seal the irrigation process with one device.

2. The lacrimal cannula of claim 1 wherein the small diameter distal tubing is narrower than 23 gauge.

3. The lacrimal cannula of claim 1 wherein said body could be composed of inert metals, precious metals, other metals, natural materials, plastics, and synthetic materials.

4. A lacrimal cannula for insertion, dilation, probing, and irrigation comprising:

means with said cannula for insertion, without prior dilation, by a narrow smooth distal tipped fluid flow tube, that prevents backwash of fluid by tapering to a larger proximal diameter tube sufficiently large enough to seal the puncta during fluid irrigation, that estimates insertion depth by this design, whereby a practitioner can dilate a lacrimal puncta, irrigate, probe, estimate insertion depth, and seal the lacrimal drainage system in one step.

* * * * *